(12) United States Patent
Huang et al.

(10) Patent No.: US 9,144,386 B2
(45) Date of Patent: Sep. 29, 2015

(54) PHYSIOLOGICAL SIGNAL DETECTION DEVICE

(75) Inventors: Hong-Hsu Huang, Taipei (TW); I-Chen Su, Taipei (TW); Shun-Tung Yang, Taipei (TW)

(73) Assignee: King's Metal Fiber Technologies Co., Ltd., Taichung (TW)

( * ) Notice: Subject to any disclaimer, the term of this patent is extended or adjusted under 35 U.S.C. 154(b) by 607 days.

(21) Appl. No.: 13/534,337

(22) Filed: Jun. 27, 2012

(65) Prior Publication Data

US 2014/0005515 A1 Jan. 2, 2014

(51) Int. Cl.
*A61B 5/04* (2006.01)

(52) U.S. Cl.
CPC .............. *A61B 5/04* (2013.01); *A61B 2562/125* (2013.01); *A61B 2562/14* (2013.01)

(58) Field of Classification Search
CPC .. A61B 5/6804; A61B 5/6805; A61B 5/0006; A61B 5/6831; A61B 5/0402; A61N 1/0484; A61N 1/0492; A61N 1/22; A61N 1/321
USPC ......... 600/372, 382, 384, 386, 388–391, 393, 600/395, 397, 508–509
See application file for complete search history.

(56) References Cited

U.S. PATENT DOCUMENTS

| | | | | | |
|---|---|---|---|---|---|
| 3,534,727 | A | * | 10/1970 | Roman | 600/389 |
| 5,236,412 | A | * | 8/1993 | Lloyd et al. | 604/20 |
| 6,065,154 | A | * | 5/2000 | Hulings et al. | 2/102 |
| 2003/0212319 | A1 | * | 11/2003 | Magill | 600/382 |
| 2004/0073104 | A1 | * | 4/2004 | Brun del Re et al. | 600/372 |
| 2007/0073131 | A1 | * | 3/2007 | Ryu et al. | 600/388 |
| 2009/0227856 | A1 | * | 9/2009 | Russell et al. | 600/388 |
| 2010/0191090 | A1 | * | 7/2010 | Shin et al. | 600/388 |
| 2010/0317954 | A1 | * | 12/2010 | Jeong et al. | 600/372 |

* cited by examiner

*Primary Examiner* — Joseph Stoklosa
*Assistant Examiner* — Brian M Antiskay
(74) *Attorney, Agent, or Firm* — Bacon & Thomas, PLLC

(57) ABSTRACT

A physiological signal detection device includes at least one electrode pad, a base layer, and at least one water absorption unit. The electrode pad is positioned on a top surface of the base layer. The electrode pad and the base layer form a first receiving compartment therebetween. The water absorption unit is positioned in the first receiving compartment. The water absorption unit has a top engaging the electrode pad, and the water absorption unit has a bottom engaging the base layer.

19 Claims, 12 Drawing Sheets

PHYSIOLOGICAL SIGNAL DETECTION DEVICE

FIELD OF THE INVENTION

The present invention relates to an improved physiological signal detection device, and in particular to a physiological signal detection device that provides water-absorbing and wet-keeping functions to wet an electrode pad for engagement with a surface of human body in order to facilitate conductive performance for detecting physiological signal and be applicable to detection of physiological signals of human body in a dry area.

BACKGROUND OF THE INVENTION

Nowadays, to detect physiological signals of human body, such as heart beat and brain wave, a plurality of electrode pads of physiological detection equipment is attached to (or worn on) various sites on a surface of human body (also referred to as body surface). These electrode pads detect the current that spreads to the peripheral tissues or body surface occurring when nervous impulses (namely variation of membrane potential) passes through human body organs (such as heart and head). The current is then transmitted by electrical wires to the physiological detection equipment to be converted into data to be displayed. In this way, the condition of an inspected portion (such as heart rate and variation of brain wave) can be realized.

The conventional electrode pad has a structure comprising a base layer (such as a layer of conductive adhesive) and an electrically conductive portion bonded to the base layer. To use in inspecting physiological signals, the body surface (such as skin) is made wet by the stickiness of the base layer or through additional application of a layer of aqueous gel that is electrically conductive in order to help the current on the body surface to flow through the base layer, the electrically conductive portion, and the electrical wires to the physiological detection equipment. On the other hand, to carry out electrotherapy, electrical current is transmitted from the physiological detection equipment to the body surface to penetrate into the body surface to simulate the portion to be treated.

However, the base layer of the conventional electrode pad, as well as the aqueous gel used in combination therewith, is generally not air permeable and may often cause allergy, and thus resulting in uncomfortableness of use. Further, skin chips (for example in condition of dry skin) and grease (in condition of oily skin) are often generated on the human body surface and may easily get stuck to the base layer and interferes with conduction of electrical current. Further, human body has body temperature, which may often causes loss (evaporation) of body surface humidity, or the gel used may get dried and is no longer capable of a humid condition, leading to separation of the adhesive from the base layer. This also interferes with the conduction of electrical current and makes it hard to detect physiological signals. Particularly in a dry condition, the humidity is even harder to keep and interruption of detection results. It may also cause cracking of the base layer.

Further, when multiple conventional electrode pads are used, if these conventional electrode pads are placed too close to each other, then they may get contact with each other and short-circuit may result.

In view of these problems, the present invention aims to provide an improved physiological signal detection device that comprises water-absorbing and wet-keeping electrical pads and is set in engagement with surface of human body to improve electrical conduction for physiological signal detection and to facilitate use in a dry area to detect physiological signals of an inspection subject and to increase convenience of use.

SUMMARY OF THE INVENTION

An object of the present invention is to provide an improved physiological signal detection device that has water-absorbing and wet-keeping functions to prevent fast loss of water and help wetting an electrode pad to thereby improve electrical conduction for physiological signal detection and facilitate use in a dry area to detect physiological signals of an inspection subject and to increase convenience of use.

Another object of the present invention is to provide an improved physiological signal detection device that comprises an edge enclosure to provide the functions of positioning and improving comfortableness and aesthetics and also reduce the influence thereof to conduction of electrical current and also reduce noise interference.

A further object of the present invention is to provide an improved physiological signal detection device that forms distinct projections after absorbing water so as to be easy to attach to and securely bond to human body surface.

To realize the above objects, the present invention provides a physiological signal detection device that comprises a base layer, at least one electrode pad, which is positioned on a top surface of the base layer, he electrode pad and the base layer forming a first receiving compartment therebetween, and at least one water absorption unit, which is positioned in the first receiving compartment. The water absorption unit has a top engaging the electrode pad, and the water absorption unit has a bottom engaging the base layer. As such, water absorbing and wet keeping functions are achieved, by which fast loss of water is prevented and wetting of the electrode pad is enhanced. Further, the water absorption unit is capable of bulging by absorbing water to raise the electrode pad, so that the electrode pad is capable of easy contact and tight engagement with human body surface to ease the detection of physiological signal of an inspection subject and improve convenience of use. Further, an edge enclosure band is also included to provide a function of positioning, improving comfortableness and aesthetics, and reducing influence on conduction of electrical current and lowering noise interference.

BRIEF DESCRIPTION OF THE DRAWINGS

The present invention will be apparent to those skilled in the art by reading the following description of preferred embodiments thereof with reference to the drawings, in which.

DETAILED DESCRIPTION OF THE PREFERRED EMBODIMENTS

Figure 1:
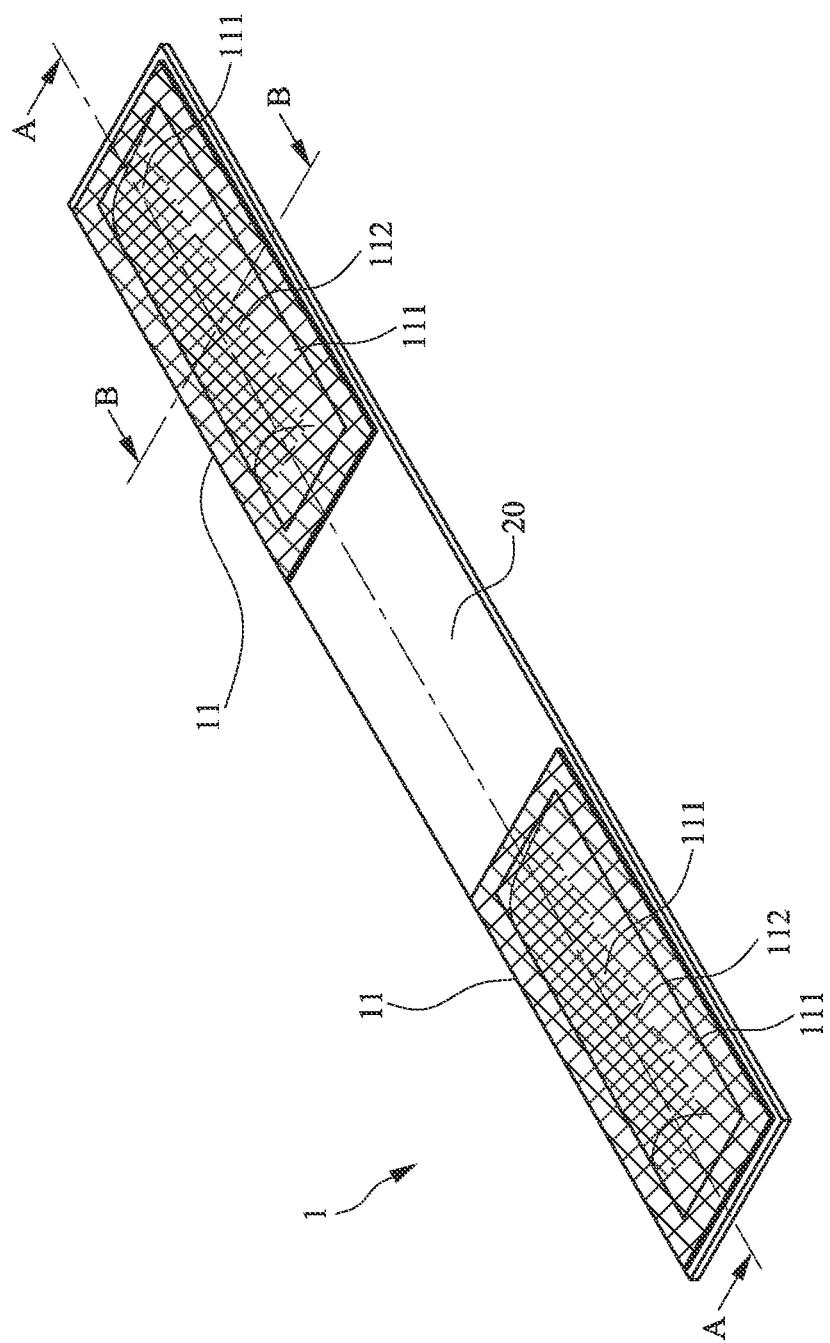
FIG. 1 is a perspective view showing a physiological signal detection device according to the present invention.

With reference to the drawings and in particular to FIGS. 1-11, an improved physiological signal detection device 1 according to the present invention comprises a combination of at least one electrode pad 11, a base layer 20, and at least one water absorption unit 30. The electrode pad 11 functions to set in contact with a surface of a portion of human body to be inspected. The water absorption unit 30 is arranged to correspond to the electrode pad 11. The base layer 20 is directly attachable to a wearable article (such as garment 50 of FIG. 12).

Figure 7:
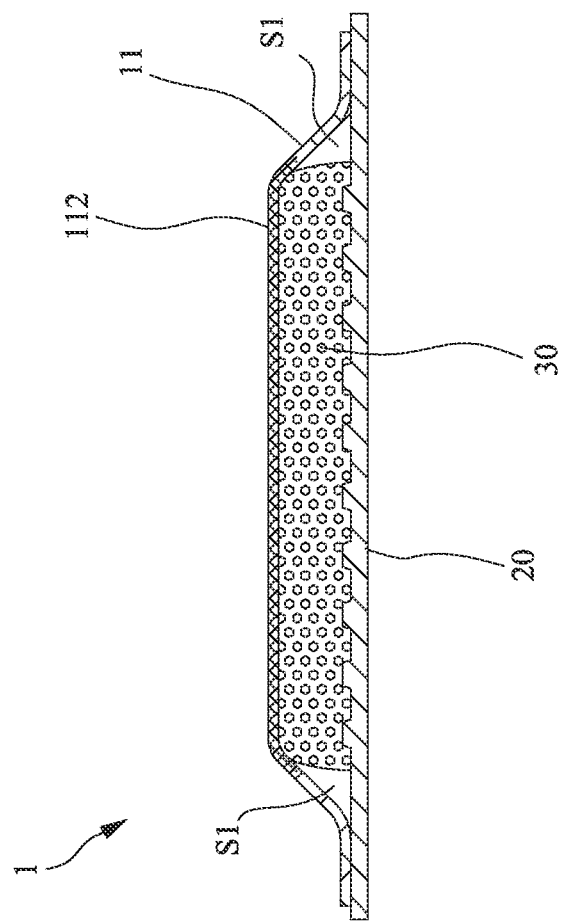
FIG. 7 is a schematic view showing a simple structure of the physiological signal detection device according to the present invention.

A simple structure of embodiment of the physiological signal detection device 1 according to the present invention is illustrated in FIG. 7, which is embodied in the form of a single electrode pad 11. The electrode pad 11 is positioned on a top surface of the base layer 20 in such a way that the electrode pad 11 and the base layer 20 form therebetween a first receiving compartment S1. The water absorption unit 30 is positioned in the first receiving compartment S1. The water absorption unit 30 has a top engaging the electrode pad 11 and a bottom engaging the base layer 20, in order to provide the present invention with a function of water absorption and thus help wetting the electrode pad 11 with the water absorption unit 30.

Figure 12:
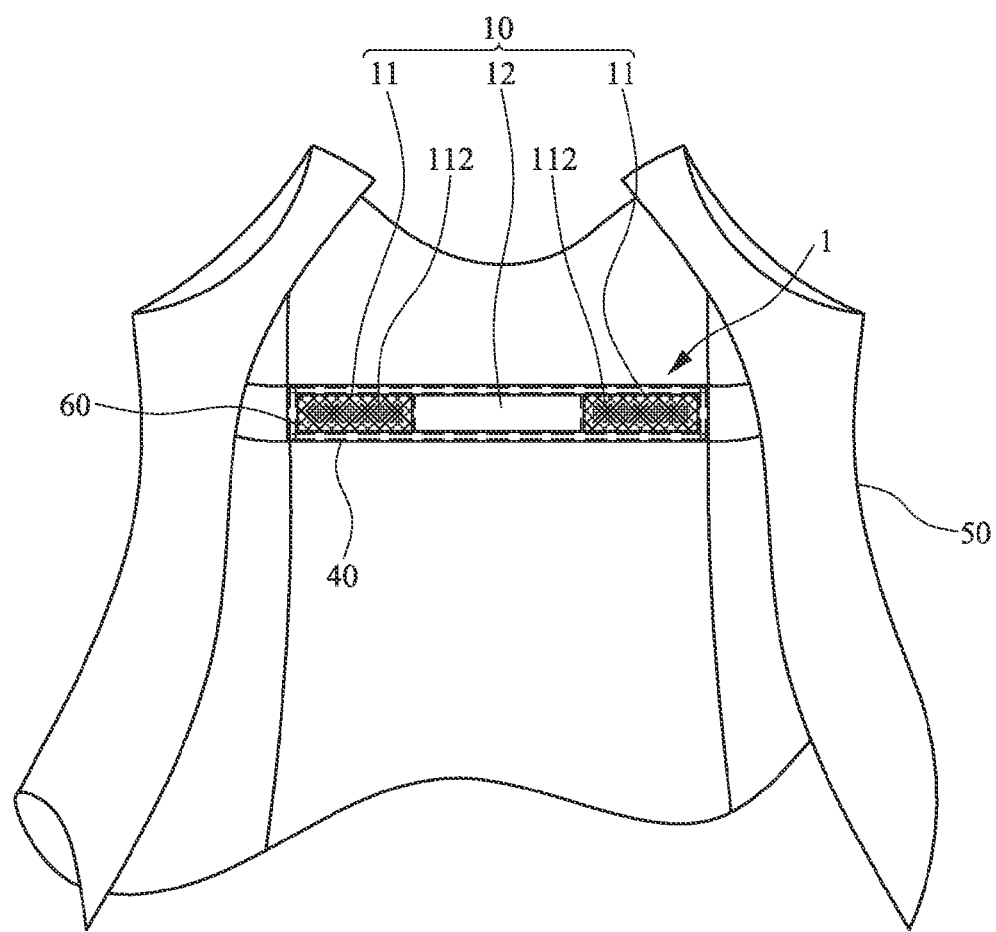
FIG. 12 is a front view showing the physiological signal detection device according to the present invention coupled to a front-open garment.

To actually practice the present invention, the physiological signal detection device 1 according to the present invention can be embodied in various formed according the number of electrode pads 11 used. For an embodiment in which the present invention is embodied with a single electrode pad 11, a wearable article (such as a wrist band or a wrist protector, not shown) to which the physiological signal detection device 1 according to the present invention is combined, is worn on a wrist of a human body, and an electronic device (such as a multimedia playing device, not shown) is also included, with an opposite end of the electronic device being electrically connected to an accessory (such as an earphone, not shown) that is attached to another portion of human body (such as an ear) for grounding (or negative electric pole) purposes so as to form a detection circuit. For an embodiment in which the present invention is embodied with a plurality of electrode pads 11, the physiological signal detection device 1 of the present invention is not limited to being mounted to wrist and may, as shown in FIG. 12, be coupled to a garment 50 in such a way that two electrode pads 11 that are mounted inside the garment 50 form a detection circuit.

The electrode pad 11 is formed by weaving a plurality of non-conductive fibrous yarns and a plurality of conductive fibrous yarns. The plurality of non-conductive fibrous yarns and the plurality of conductive fibrous yarns are interwoven to form therebetween a plurality of mesh pores 111. The plurality of conductive fibrous yarns of the electrode pad 11 is woven to form a conductive zone 112 by which contact area is increased. The electrode pad 11 uses the plurality of mesh pores 111 to facilitate penetration of conductive substance (such as water and normal saline) in order to improve conduction of electrical current and also to block foreign objects, such as dusts, from penetrating into the electrode pad 11 for easing subsequent cleaning operation (removing the foreign objects) and maintenance and reducing interference with the conductive zone 112 and minimizing generation of noise and facilitating the water absorption unit 30 absorbing penetrating water to also achieve the function of wet keeping. In the embodiment, the electrode pad 11 is entirely made by weaving a plurality of conductive fibrous yarns to make the entire electrode pad 11 conductive thereby help improving the use for detection.

Figure 2:
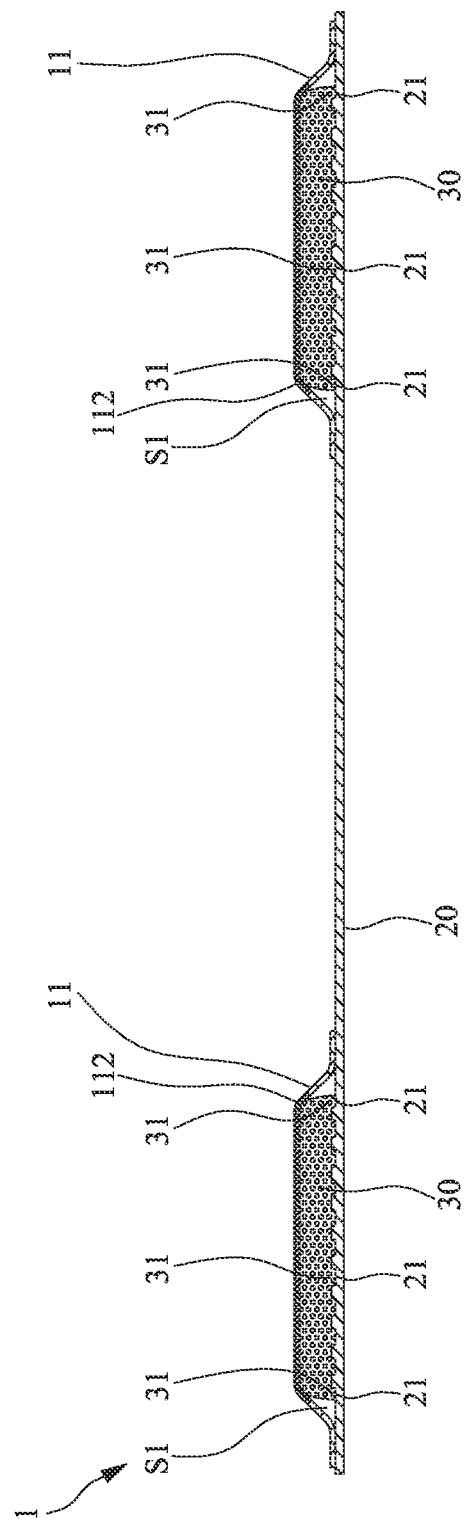
FIG. 2 is a cross-sectional view taken along line A-A of FIG. 1.
Figure 3:
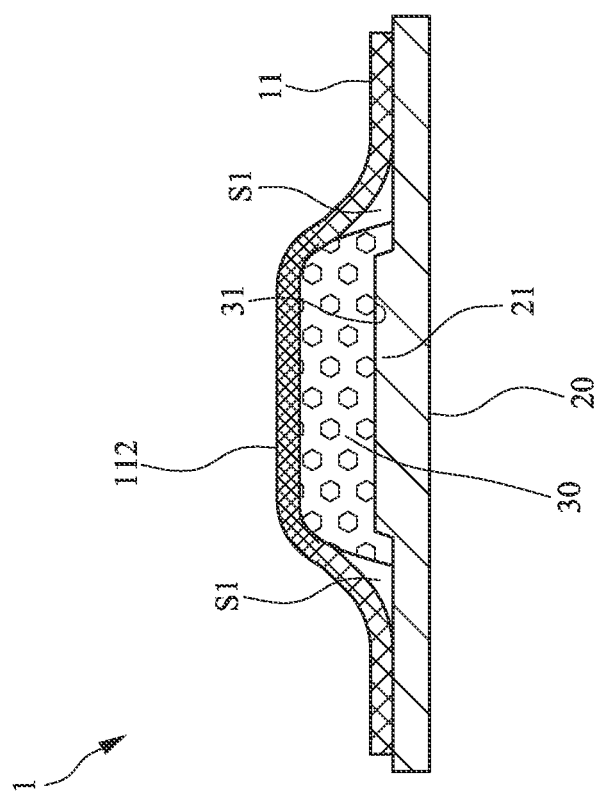
FIG. 3 is a cross-sectional view, in an enlarged form, taken along line B-B of FIG. 1.

To make the water absorption unit 30 corresponding to and uniformly engaging and thus wetting the electrode pad 11, as shown in FIGS. 2 and 3, the water absorption unit 30 forms in a bottom thereof a plurality of spaced anti-skidding sections 31 (such as ribs or grooves). The base layer 20 forms, in the top surface thereof, a plurality of spaced counterpart anti-skidding sections 21 (such as grooves or ribs). The counterpart anti-skidding sections 21 respectively correspond to the anti-skidding sections 31. The counterpart anti-skidding sections 21 are respectively engageable with the anti-skidding sections 31 in order to make each water absorption unit 30 stably standing in each first receiving compartment S1 and prevent uneven raised configuration on an outside surface of the electrode pad 11 due to sliding of the water absorption unit 30. In an actual way of practicing the present invention, the counterpart anti-skidding sections 21 can be ribs, while the anti-skidding sections 31 are grooves that are engageable with the ribs.

The water absorption unit 30 is a component made of cotton paper, cotton fabric, silica gel, water-absorbing foam, fluff paste (such as pulp), sodium polyacrylate, or other polymers of propenoic acid that show an equivalent function, or can be embodied as a member of superabsorbent polymers showing an equivalent function. In manufacture, the types used can be increased for easy replacement and avoiding unnecessary constraint to a single type of material.

The water absorption unit 30 is an elastic body having a shape that follows an actual manufacturing process to be a sphere (or a block) for easy manufacturing and to make the water absorption unit 30 of the present invention showing elasticity to be expandable or compressible for easy bending or folding and may resume the original shape thereafter so as to easily comply with the curve of surface of human body when attached to the surface of human body thereby facilitating easy use and replacement.

Figure 4:
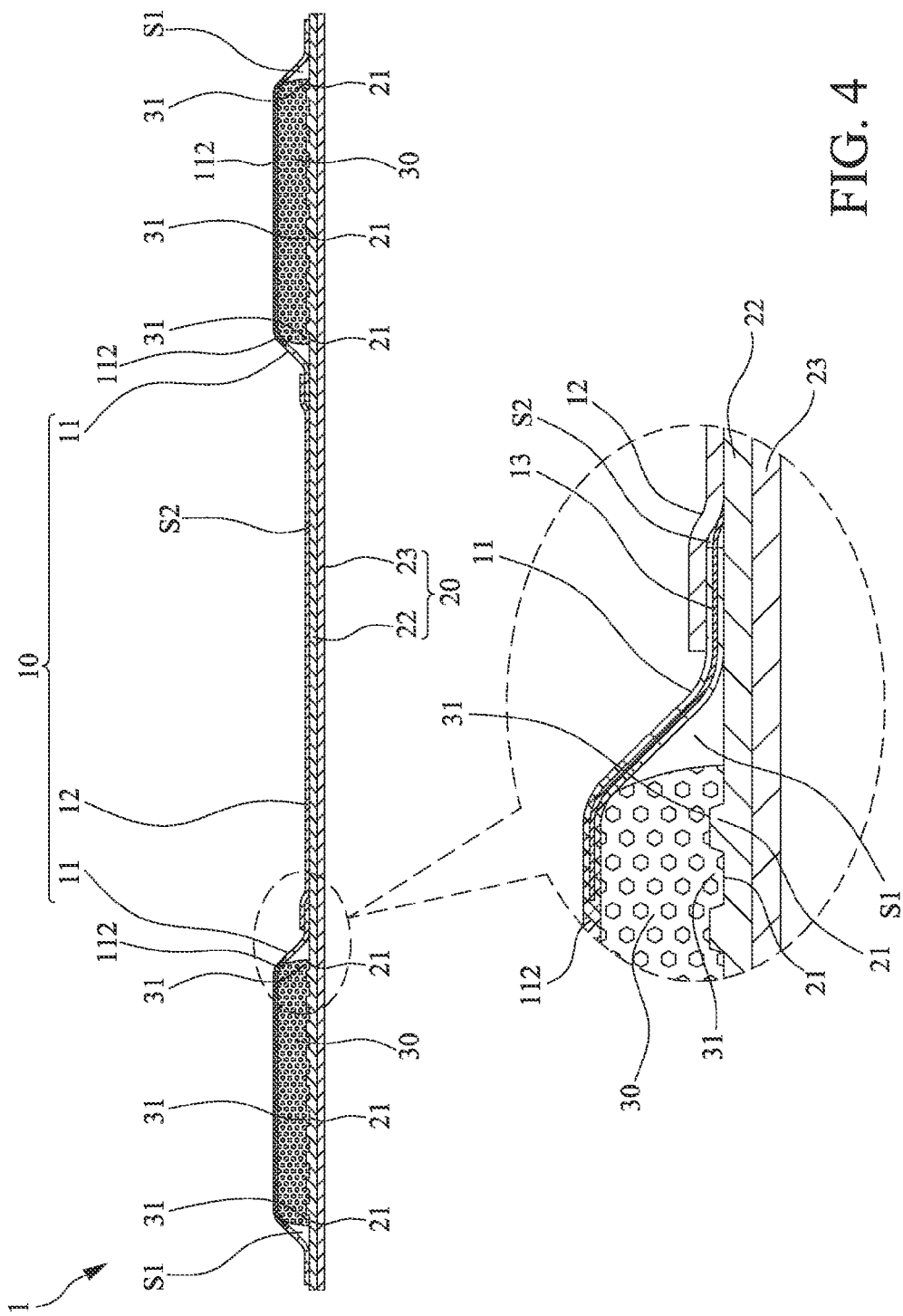
FIG. 4 is a schematic view showing each electrode pad of the physiological signal detection device shown in FIG. 2 is provided with extension conductor and a base layer being formed of an upper water-penetrating layer and a lower water-proof layer overlapping each other.

The base layer 20 may comprise a fabric layer or a water-proof layer. In an embodiment where the base layer 20 is made of a fabric layer, the present invention shows air penetrateability for the entirety thereof. On the other hand, the water absorption unit 30 is confined in the first receiving compartment S1 so that water (or humidity), when passing through the electrode pad 11 (or the base layer 20), can be re-absorbed by the water absorption unit 30 so as to effectively prevent water (humidity) from easily flowing out of the physiological signal detection device 1 for continuous wetting the electrode pad 11 for keeping a long period of time of conduction of electrical current. For an embodiment where the base layer 20 is made of a water-proof layer, manufacture can be done with plastic sheet or polyester fiber to provide a water-proof function and prevent loss of water (humidity) through the base layer 20 and also showing a function of wet keeping. However, the base layer 20 of the present invention is not limited to these and as shown in FIG. 4, the base layer 20 may comprises an upper water-proof layer 22 and a lower fabric layer 23. The upper water-proof layer 22 (made of polyester fiber) contacts each water absorption unit 30 and provides a water-proof function. The lower fabric layer 23 protects the upper water-proof layer 22. The upper water-proof layer 22 has a top surface that forms the previously discussed counterpart anti-skidding sections 21, while the lower fabric layer 23 is attachable to a garment.

Further, in the instant embodiment, the at least one electrode pad 11 can be a plurality of electrode pads 11, and the at least one water absorption unit 30 can be a plurality of water absorption units 30. The term "a plurality of" refers to a number that is equal to or greater than two. An example of the present invention shown in FIGS. 2 and 4 comprises two electrode pads 11 used in combination with two water absorption units 30. The two electrode pads 11 are arranged, in a mutually spaced manner, on the top surface of the base layer 20 (see FIG. 1) in such a way that each of the electrode pads 11 forms a first receiving compartment S1 with respect to the base layer 20 and the water absorption units 30 are respectively received and retained in the first receiving compartments S1. Each of the water absorption units 30 has a top in engagement with each of the electrode pads 11. Each of the water absorption units 30 has a bottom that is set in engagement with the base layer 20 to facilitate each of the water absorption units 30 to wet each of the electrode pads 11.

Figure 5:
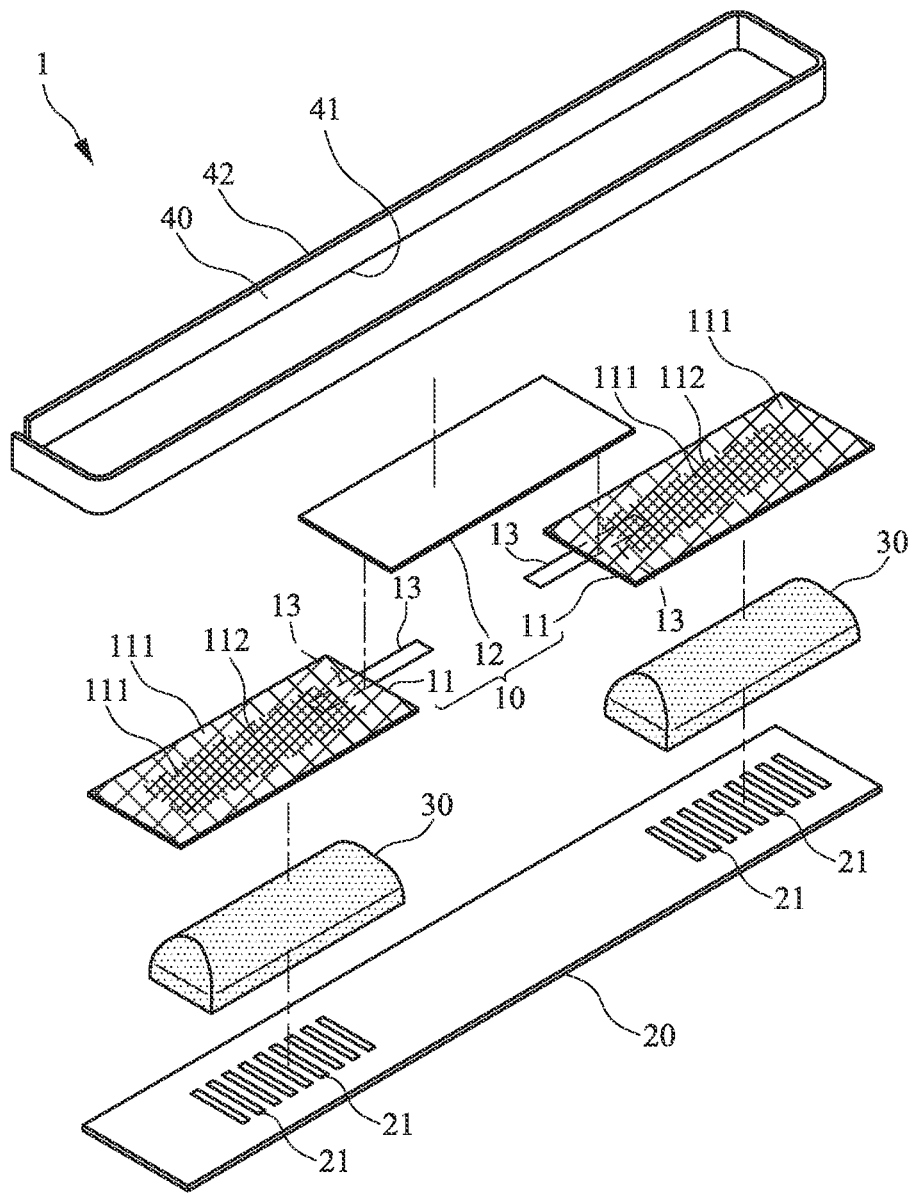
FIG. 5 is an exploded view showing the physiological signal detection device of FIG. 1 further comprising an edge enclosure band, connection band being provided between electrode pads, each electrode pad being provided with an extension conductor

Further, as shown in FIGS. 4 and 5, at least one connection band 12 is connected between any two adjacent ones of the electrode pads 11, whereby a second receiving compartment S2 is formed between the connection band 12 and the base layer 20. The electrode pads 11 and the connection band 12 are jointed together to form the top layer 10 that corresponds in shape to the base layer 20. In this way, being assisted by the connection band 12, the electrode pads 11 can efficiently attached to opposite sides of a specific portion of human body (such as left and right sides of head, left and right side parts of back, or opposite portions of chest and back of a heart-associated portion) and avoid short-circuit caused by mutual contact occurring between the electrode pads 11.

The second receiving compartment S2 functions to receive and retain other objects (such as electrical wires, sensors, and controllers). In case that no article or object is received in the second receiving compartment S2, the connection band 12 is bonded to the top surface of the base layer 20.

Further, for an electrode pad 11 of a relatively large size, to save expense and to effectively form electrical engagement between the electrode pad 11 and body surface, as shown in FIGS. 4 and 5, each of the electrode pads 11 is provided with at least one extension conductor 13 (which is particularly shown in the enlarged view at left lower corner of FIG. 4) connected thereto. The extension conductor 13 has an end extending into and electrically connected to the electrode pad 11 (namely being electrically connected to the conductive zone 112) and the extension conductor 13 has an opposite end projecting beyond an end of the electrode pad 11, whereby after each water absorption unit 30 absorbs water and bulges, each electrode pad 11 is set in a projecting condition so that easy electrical connection of the extension conductor 13 of the electrode pad 11 can be made with electrical current of the surface of human body. In a practical application, where the present invention is embodied with a single electrode pad 11, the extension conductor 13 discussed above can also be included. Further, when the present invention is embodied with more than two electrode pads 11, based on the sizes thereof, the electrode pads 11 can be selectively provided with and coupled to extension conductors 13.

The extension conductor 13 discussed above for the electrode pad 11 is formed by composing a plurality of conductive yarns that are provided for weaving purposes and are relatively flexible. The extension conductor 13 is electrically connected to an electrical wire (not shown), which has an opposite end electrically connected to physiological detection equipment (not shown), whereby electrical current of body surface flows through the electrode pad 11, the extension conductor 13, and the electrical wire to enter the physiological detection equipment. In a practical application, the extension conductor 13 is not a necessary component and the electrode pad 11 is directly and electrically connected to the electrical wire (not shown).

Figure 6:
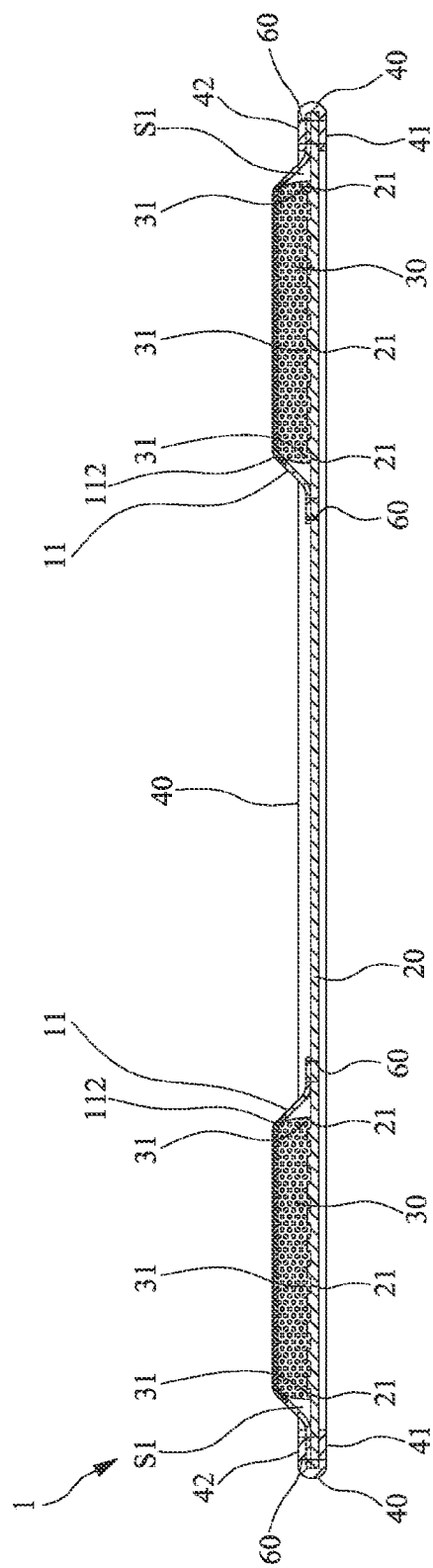
FIG. 6 is a schematic view showing the physiological signal detection device shown in FIG. 2 further comprising an edge enclosure band.

Further, as shown in FIG. 5 (in combination with FIG. 6), in a preferred embodiment, the present invention further comprises an edge enclosure band 40. The edge enclosure band 40 has a lower flange 41 that is coupled to an edge portion of a bottom surface of the base layer 20 and the edge enclosure band 40 also has an upper flange 42 that is coupled to an edge portion of a top surface of the top layer 10 (which is composed of the connected electrode pads 11 and connection band 12). The edge portion of the top surface of the top layer 10 corresponds to the edge portion of the bottom surface of the base layer 20 so as to allow the edge enclosure band 40 to effect enclosure and retention for improving comfortableness and aesthetics. In the instant embodiment, the connection band 12 is optionally provided based on the practical needs. Thus, the present invention can be embodied as shown in FIG. 6 to arrange two mutually-spaced electrode pads 11 on a top surface of the base layer 20 with the upper flange 42 of the edge enclosure band 40 being only coupled to the edge portions of top surfaces of the two electrode pads 11. In this way, when the present invention is attached to a garment 50 (see FIG. 12) by sewing, sewn area can be easily identified with the assistance of the edge enclosure band 40, whereby sewing thread 60 is applied along the edge enclosure band 40 to prevent mistakenly penetrating through the water absorption unit and thus damaging the structure. The present invention is applicable in combination with a garment 50, which, when worn by an inspection subject, allows the conductive zones 112 of the two electrode pads 11 to be quickly set corresponding to and conveniently attached, in tight engagement, to the portion to be inspected, eliminating the need for separately attaching the pads.

Figure 8:
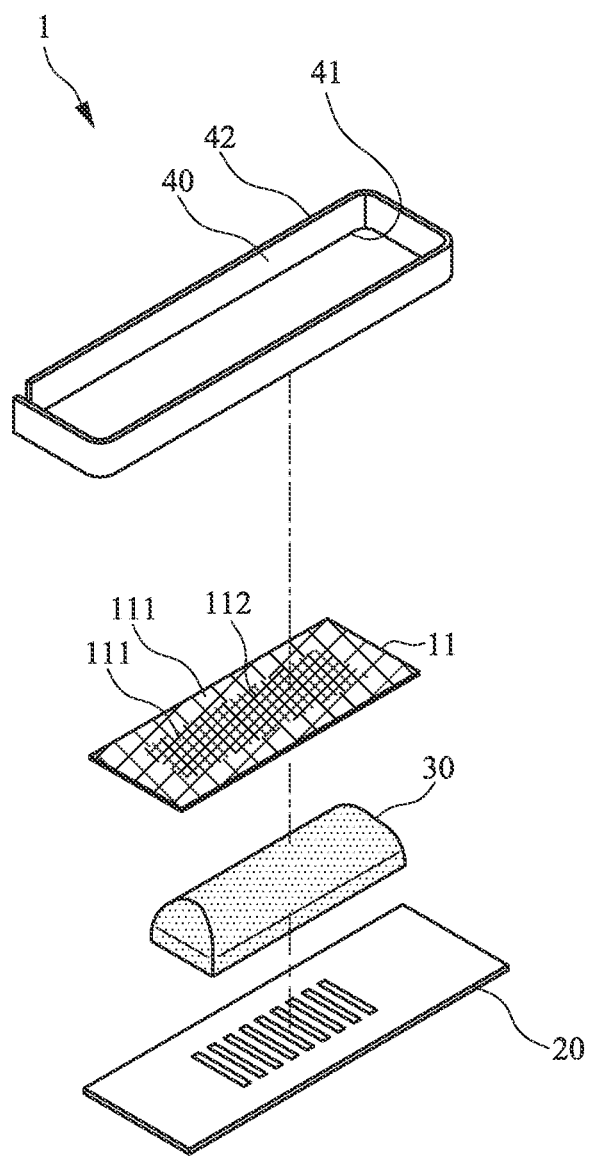
FIG. 8 is an exploded view of the physiological signal detection device shown in FIG. 7 further comprising an edge enclosure band.
Figure 9:
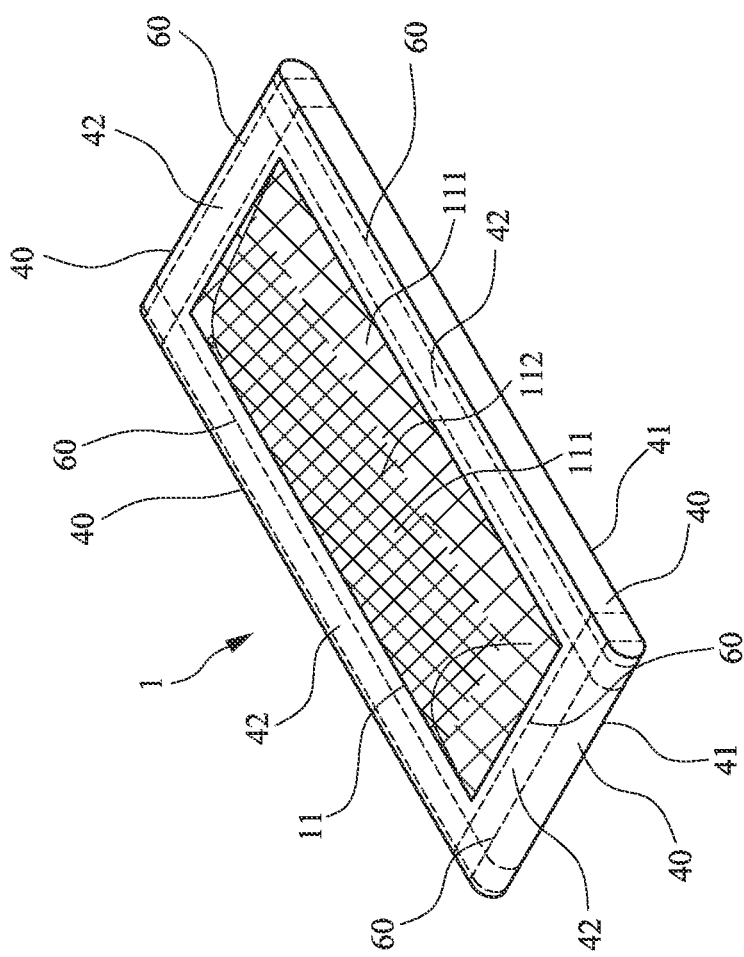
FIG. 9 is a perspective view showing the physiological signal detection device of FIG. 8 after being assembled.

Further, as shown in FIG. 8, the edge enclosure band 40 can be embodied in combination with the previously discussed simple structure embodiment of the physiological signal detection device 1 (such a simple structure embodiment being shown in FIG. 7 and a combined embodiment being shown in FIG. 9) in such a way that the lower flange 41 of the edge enclosure band 40 is coupled to an edge portion of a bottom surface of the base layer 20 and the upper flange 42 of the edge enclosure band 40 is coupled to an edge portion of a top surface of the electrode pad 11, in which the edge portion of the top surface of the electrode pad 11 corresponds to the edge portion of the bottom surface of the base layer 20 in order to facilitate enclosure and retention effected by the edge enclosure band 40 and to improve comfortableness and aesthetics and help attaching to the garment 50.

Figure 10:
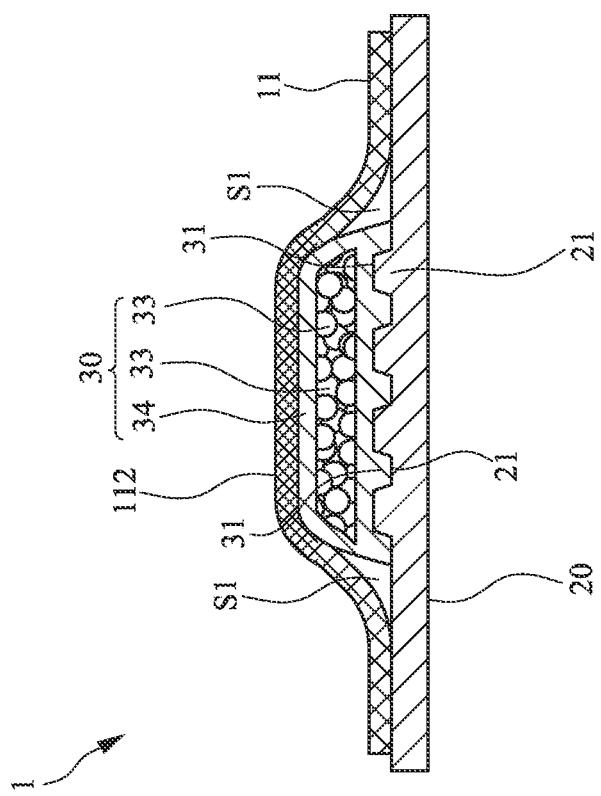
FIG. 10 is a schematic view showing an embodiment where a water absorption unit of FIG. 7 is composed of a water-preservation inner lining in combination with an accommodation sack.

Further, as shown in FIG. 10, the water absorption unit 30 may further comprises at least one water-preservation inner lining 33 and an accommodation sack 34 enclosing the water-preservation inner lining 33 in order to prevent fast loss of water. In an embodiment where a plurality of water-preservation inner linings 33 is included, to prevent a loose arrangement of the plurality of water-preservation inner linings 33, the accommodation sack 34 is used to enclose and confine the water-preservation inner linings 33 so that the water absorption unit 30 forms a structure that is adjustable and supports the electrode pad 11, this featuring both water preservation and supporting. When the present invention is attached to the human body surface, the water absorption unit 30 tightly abut against the corresponding electrode pad 11 to comply with and tightly engage with the curves of body surface, eliminating any potential gap therebetween, whereby electrical current on the body surface can be easily conducted to the electrode pad 11 to enhance the detection of variation of physiological signal.

The accommodation sack 34 has a bottom that is also provided with a plurality of spaced anti-skidding sections 31 and the top surface of the base layer 20 forms a plurality of spaced counterpart anti-skidding sections 21. The counterpart anti-skidding sections 21 respectively correspond to the anti-skidding sections 31. The counterpart anti-skidding sections 21 are respectively engageable with the anti-skidding sections 31 so as to prevent uneven raised configuration on an outside surface of the electrode pad 11 due to sliding of the water absorption unit 30.

Figure 11:
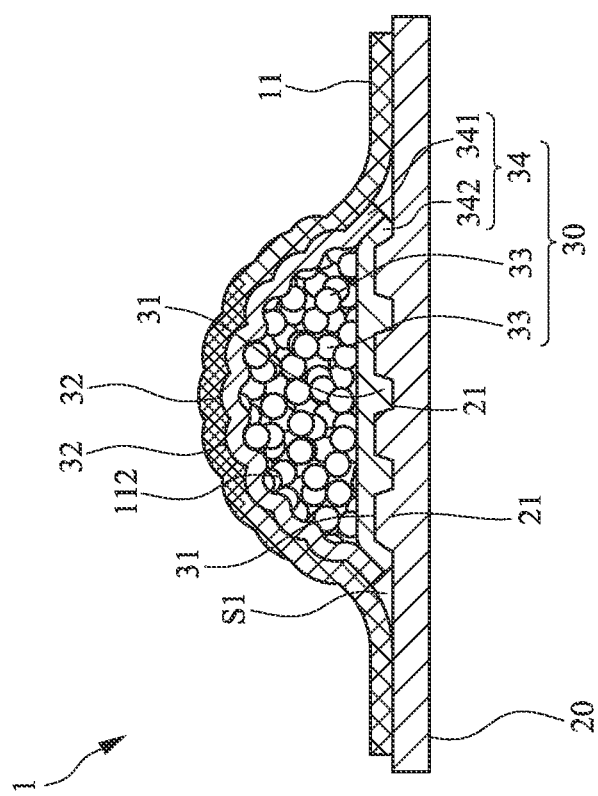
FIG. 11 is schematic view showing the accommodation sack of FIG. 10 comprises an upper water-penetrating layer and a lower water-proof layer that overlap each other and the water absorption unit absorbing water and getting bulging to show a projecting form.

To prevent the water of the water absorption unit 30 from being fast lost and to enhance wetting of the electrode pad 11 by the water absorption unit 30, as shown in FIG. 11, the accommodation sack 34 comprises an upper water-penetrating layer 341 and a lower water-proof layer 342 that overlap each other. The lower water-proof layer 342 is set in engagement with the base layer 20 and the upper water-penetrating layer 341 is in engagement with the electrode pad 11. The plurality of anti-skidding sections 31 is formed on a bottom surface of the lower water-proof layer 342. The upper water-penetrating layer 341 is a fabric layer, paper layer, or semi-permeable membrane resin layer. As such, water is only allowed to discharge through the accommodation sack 34' and the electrode pad 11 and this facilitates keeping water in the accommodation sack 34.

The water-preservation inner lining 33 is a component made of cotton paper, cotton fabric, silica gel, water-absorbing foam, fluff paste, sodium polyacrylate or other polymers of propenoic acid that show an equivalent function, or super-absorbent polymers. The shape of the component can be variable forms (such as sphere).

In the above discussion, the water absorption unit 30 has a top that is directly shaped as a projecting form (as shown in FIG. 8) and after absorbing water, the water absorption unit 30 bulges and shows a more distinctly projecting form to directly support the electrode pad 11. As shown in FIG. 11, if the water absorption unit 30 is made in the form comprising a plurality of water-preservation inner linings 33 in combination with an accommodation sack 34, then the water-preservation inner linings 33, after absorbing water, become bulging to make a plurality of projecting portions 32 on the surface of the accommodation sack 34. Such projecting portions 32 are also capable of supporting the corresponding electrode pad 11 and this makes it more compliant to the curves of body surface for more tight engagement.

As such, the present invention provides a physiological signal detection device, which comprises a combined structure of at least one electrode pad 11, a base layer 20, and at least one water absorption unit 30 to provide water absorbing and wet keeping functions, by which fast loss of water is prevented and wetting of the electrode pad 11 is enhanced. Further, the water absorption unit 30 is capable of bulging by absorbing water to show a projecting form, so that an effect of easy contact and tight engagement of the electrode pad with human body surface is achieved to ease the detection of physiological signal of an inspection subject and improve convenience of use. Further, an edge enclosure band 40 is also included to provide function of positioning, improving comfortableness and aesthetics, and reducing influence on conduction of electrical current and lowering noise interference.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A physiological signal detection device, comprising: a base layer; at least one electrode pad, which is positioned on a top surface of the base layer, the electrode pad and the base layer forming a first receiving compartment therebetween; and at least one water absorption unit, which is positioned in the first receiving compartment, the water absorption unit having a top engaging the electrode pad, the water absorption unit having a bottom engaging the base layer; wherein the water absorption unit comprises at least one water-preservation inner lining and an accommodation sack enclosing the water-preservation inner lining, the accommodation sack having a bottom forming a plurality of spaced anti-skidding sections, the top surface of the base layer forming a plurality of spaced counter anti-skidding sections, the counterpart anti-skidding sections respectively corresponding to the anti-skidding sections, the counterpart anti-skidding sections being respectively engageable with the anti-skidding sections, wherein the anti-skidding sections are ribs or grooves.

2. The physiological signal detection device as claimed in claim 1, wherein the electrode pad is formed by weaving a plurality of non-conductive fibrous yarns and a plurality of conductive fibrous yarns, the plurality of conductive fibrous yarns of the electrode pad being woven to form a conductive zone.

3. The physiological signal detection device as claimed in claim 1, wherein the electrode pad is entirely made by weaving a plurality of conductive fibrous yarns.

4. The physiological signal detection device as claimed in claim 1, wherein the water absorption unit forms in a bottom thereof a plurality of spaced anti-skidding sections, the base layer forming, in the top surface thereof, a plurality of spaced counterpart anti-skidding sections, the counterpart anti-skidding sections respectively corresponding to the anti-skidding sections, the counterpart anti-skidding sections being respectively engageable with the anti-skidding sections.

5. The physiological signal detection device as claimed in claim 1, wherein the water absorption unit comprises one of cotton paper, cotton fabric, silica gel, and water-absorbing foam.

6. The physiological signal detection device as claimed in claim 1, wherein the water absorption unit comprises a component made of sodium polyacrylate.

7. The physiological signal detection device as claimed in claim 1, wherein the projection comprises an elastic object.

8. The physiological signal detection device as claimed in claim 1, wherein the base layer comprises a fabric layer.

9. The physiological signal detection device as claimed in claim 1, wherein the base layer comprises a water-proof layer.

10. The physiological signal detection device as claimed in claim 1, wherein the base layer comprises an upper water-penetrating layer and a lower water-proof layer that overlap each other, the upper water-penetrating layer being set in engagement with the water absorption unit.

11. The physiological signal detection device as claimed in claim 1, wherein the at least one electrode pad includes a plurality of electrode pads, which are arranged, in a mutually spaced manner, on the top surface of the base layer, each of the electrode pads and the base layer forming therebetween a first receiving compartment, the at least one water absorption unit including a plurality of water absorption units, each of the water absorption units being positioned in each of the first receiving compartments, each of the water absorption units having a top engaging each of the electrode pads, each of the water absorption units having a bottom engaging the base layer, a connection band being connected to two adjacent ones of the electrode pads, the connection band and the base layer forming therebetween a second receiving compartment, the electrode pads and the connection band being connected to each other to form a top player corresponding in shape to the base layer.

12. The physiological signal detection device as claimed in claim 7 further comprising an edge enclosure band, which has a lower flange coupled to an edge portion of the bottom surface of the base layer and an upper flange coupled to an edge portion of the top surface of the top layer, the edge portion of the top surface of the top layer corresponding to an edge portion of a bottom surface of the base layer.

13. The physiological signal detection device as claimed in claim 11, wherein each of the electrode pads is further provided with at least one extension conductor, which has an end extending into and electrically with each of the electrode pads and an opposite end extending beyond one side of each of the electrode pads.

14. The physiological signal detection device as claimed in claim 1 further comprising an edge enclosure band, the edge enclosure band having a lower flange coupled to an edge portion of a bottom surface of the base layer and an upper flange coupled to an edge portion of a top surface of the electrode pad, the edge portion of the top surface of the electrode pad corresponding to the edge portion of the bottom surface of the base layer.

15. The physiological signal detection device as claimed in claim 1, wherein the water-preservation inner lining comprises one of cotton paper, cotton fabric, silica gel, and water-absorbing foam.

16. The physiological signal detection device as claimed in claim 1, wherein the water-preservation inner lining comprises a component made of sodium polyacrylate.

17. The physiological signal detection device as claimed in claim 1, wherein the accommodation sack comprises an upper water-penetrating layer and a lower water-proof layer that overlap each other, the lower water-proof layer being set in engagement with the base layer, the upper water-penetrating layer being set in engagement with the electrode pad, the plurality of anti-skidding sections being formed on a bottom surface of the lower water-proof layer.

18. The physiological signal detection device as claimed in claim 17, wherein the upper water-penetrating layer comprises one of a fabric layer, a paper layer, or a semi-permeable membrane resin layer.

19. The physiological signal detection device as claimed in claim 1, wherein the water absorption unit shows a projecting form.

\* \* \* \* \*